United States Patent
Klyber (10) Patent No.: US 11,419,980 B2
(45) Date of Patent: Aug. 23, 2022

(54) BOLUS REFILL INDICATOR

(71) Applicant: Avent, Inc., Alpharetta, GA (US)

(72) Inventor: Travis W. Klyber, Roswell, GA (US)

(73) Assignee: Avent, Inc., Alpharetta, GA (US)

(*) Notice: Subject to any disclaimer, the term of this patent is extended or adjusted under 35 U.S.C. 154(b) by 599 days.

(21) Appl. No.: 16/308,139

(22) PCT Filed: Jun. 24, 2016

(86) PCT No.: PCT/US2016/039164
§ 371 (c)(1),
(2) Date: Dec. 7, 2018

(87) PCT Pub. No.: WO2017/222543
PCT Pub. Date: Dec. 28, 2017

(65) Prior Publication Data
US 2019/0217009 A1     Jul. 18, 2019

(51) Int. Cl.
*A61M 5/168*     (2006.01)
*A61M 5/14*     (2006.01)

(52) U.S. Cl.
CPC .......... *A61M 5/16813* (2013.01); *A61M 5/14* (2013.01); *A61M 2005/1405* (2013.01);
(Continued)

(58) Field of Classification Search
CPC .. A61M 5/16813; A61M 5/14; A61M 5/1424; A61M 5/16831; A61M 5/16877;
(Continued)

(56) References Cited

U.S. PATENT DOCUMENTS 5,084,021 A   1/1992   Baldwin
5,891,102 A   4/1999   Hiejima et al.
(Continued)

FOREIGN PATENT DOCUMENTS

GB    2 413 024 A    10/2005
WO    WO 2012/175503 A1    12/2012
(Continued)

OTHER PUBLICATIONS

Tudorza Pressair, obtained from https://www.drugs.com/pro/tudorza-pressair.html, 2018, 30 pages.
(Continued)

*Primary Examiner* — Nathan R Price
*Assistant Examiner* — Anh Bui
(74) *Attorney, Agent, or Firm* — Meunier Carlin & Curfman LCC (57) ABSTRACT

A drug administration device including a push button, plunger, housing extending in an axial direction to define top and bottom ends, and bolus refill indicator is provided. The indicator is disposed on the plunger and visible through a window in the housing. The indicator can include a first section having a first color located towards the top end of the housing, a second section having a second color located towards the bottom end of the housing, and a third section disposed therebetween including a gradient between the first and second colors. Alternatively, the indicator can include a line extending in a direction perpendicular to the axial direction. The housing includes a first indicator reference point that is a first color and aligned with a bottom of the indicator window and a second indicator reference point that is a second color and aligned with a top of the indicator window.

17 Claims, 9 Drawing Sheets

(52) U.S. Cl.
CPC ............... *A61M 2205/3379* (2013.01); *A61M 2205/584* (2013.01)

(58) Field of Classification Search
CPC .... A61M 2205/3379; A61M 2205/584; A61M 2005/1405; A61M 2005/14208
See application file for complete search history.

(56) References Cited

U.S. PATENT DOCUMENTS

| | | | |
|---|---|---|---|
| 6,213,981 B1 | 4/2001 | Hiejima et al. | |
| 6,936,035 B2 | 8/2005 | Rake et al. | |
| 8,425,469 B2 | 4/2013 | Jacobson | |
| 8,439,862 B2 | 5/2013 | Massengale | |
| 8,567,394 B2 | 10/2013 | Herder | |
| 8,578,934 B2 | 11/2013 | Morton et al. | |
| 8,591,463 B1 | 11/2013 | Cowe | |
| 8,753,308 B2 | 6/2014 | Palmer et al. | |
| 8,808,269 B2 | 8/2014 | Bazargan | |
| 8,869,735 B2 | 10/2014 | Lu | |
| 2004/0127860 A1* | 7/2004 | Rake | A61M 5/14216 604/246 |
| 2005/0161467 A1 | 7/2005 | Jones | |
| 2007/0156090 A1 | 7/2007 | Kriesel | |
| 2012/0157918 A1 | 6/2012 | Valle et al. | |
| 2012/0310169 A1 | 12/2012 | Sonderegger et al. | |
| 2012/0312301 A1 | 12/2012 | Allsop | |
| 2013/0336814 A1 | 12/2013 | Kamen et al. | |
| 2014/0046288 A1 | 2/2014 | Geipel et al. | |
| 2014/0276415 A1 | 9/2014 | Davis et al. | |
| 2015/0000657 A1 | 1/2015 | Herder et al. | |
| 2015/0037772 A1 | 2/2015 | Julian et al. | |
| 2015/0053305 A1 | 2/2015 | Davidian et al. | |
| 2015/0066206 A1 | 3/2015 | Patel et al. | |
| 2015/0265777 A1* | 9/2015 | Whitley | A61B 17/3474 604/512 |
| 2016/0129195 A1* | 5/2016 | Jennings | A61M 5/31586 604/198 |

FOREIGN PATENT DOCUMENTS

| | | |
|---|---|---|
| WO | WO 2014/111370 A1 | 7/2014 |
| WO | WO 2014/198798 A2 | 12/2014 |
| WO | WO 2015/036346 A1 | 3/2015 |
| WO | WO 2015/069638 A1 | 5/2015 |
| WO | WO 2016/025316 A1 | 2/2016 |

OTHER PUBLICATIONS

International Search Report and Written Opinion for PCT/US2016/039164, dated Mar. 20, 2017, 11 pages.

\* cited by examiner

BOLUS REFILL INDICATOR

RELATED APPLICATION

The present application is the national stage entry of and claims priority to International Patent Application No. PCT/US2016/039164, filed on Jun. 24, 2016, the entire contents of which are incorporated herein by reference.

FIELD OF THE INVENTION

The present invention relates to a bolus refill indicator for use with a patient controlled drug administration device.

BACKGROUND OF THE INVENTION

The treatment of pain symptoms, e.g., post-operative pain or pain resulting from disease or injury, frequently entails the subcutaneous and/or intravenous ("IV") infusion of a liquid analgesic and/or anesthetic drug into the patient, e.g., by one or more hypodermic injections thereof. When pain is more chronic, it may be preferable to catheterize the patient intravenously, such as with a hypodermic needle, and infuse the drug through the catheter continuously at a low, or "basal," rate of flow using an "IV drip" or an electromechanical pump having an adjustable low flow rate.

Many patients who exhibit chronic pain symptoms also experience periodic episodes in which the pain level is perceived as much more acute, indicating a need for a temporarily greater infusion rate of the drug. To effect this, it is necessary to adjust the flow rate of the infusion apparatus, which in turn, necessitates the presence and intervention by a trained health care professional, as the patient typically lacks the training, skill and/or physical ability to effect such an adjustment of the infusion device.

In light of the foregoing, there have been a number of proposals for a "Patient Controlled Analgesic," or "PCA," drug administration device that would enable a patient to self-administer a drug intravenously without intervention by a health care professional at, for instance, the onset of an acute pain episode, that is not only simple and effortless to operate, but is also failsafe in use to preclude the possibility of a self-administered drug overdose. Examples of such PCA devices can be found in U.S. Pat. No. 5,084,021 to B. Baldwin; U.S. Pat. No. 5,891,102 to K. Hiejima et al.; and U.S. Pat. No. 6,213,981 to K. Hiejima et al.

These devices all have in common the provision of a reciprocating pump in which the patient manually effects a "compression" stroke of the pump by depressing a plunger of the pump, thereby expressing a measured bolus of a liquid drug to the patient intravenously, after which a compression spring and/or a pressurized source of the drug returns the plunger to its initial position, thereby effecting a refill, or "intake," stroke of the pump. The rate at which the pump refills, and hence, the rate at which the patient may self-administer the drug, is limited by a flow restrictor placed at the inlet of the pump. A reverse flow of fluids from the patient to the pump may be effected by a check valve disposed at the outlet of the pump.

While the foregoing PCA devices afford a partial solution to the problem of a patient controlled drug administration device, they also include certain drawbacks. For example, some require that the patient continuously exert a force on the plunger throughout the compression stroke of the pump, which may take several seconds or even minutes to complete, and some patients may not be physically capable of such a prolonged exertion. Others require that the patient push a first button down on the pump to effect the compression stroke, then push a second button on the pump to initiate the intake stroke, which may also be of prolonged duration, after the compression stroke is complete, which requires that the patient monitor the position of the plunger to know when to push the second button.

U.S. Pat. No. 6,936,035 to K. Rake et al. addresses these drawbacks and describes a PCA device that can administer either or both of a continuous and a bolus infusion of a liquid drug to a patient, in which the bolus doses can be safely self-administered by the patient by quickly depressing a single button, to effect the compression stroke of the pump, and which thereafter automatically initiates the intake stroke of the pump when the compression stroke is completed. However, after the bolus infusion of the liquid drug to the patient is completed, it may be difficult for the patient to know when a new bolus of the liquid drug is available for administration. Thus, the patient may depress the button on the PCA device before the pump has been refilled, resulting in the delivery of only a partial bolus to the patient. While the PCA device of U.S. Pat. No. 6,936,035 to K. Rake et al. does include a window through which an indicator is visible, a need exists for an improved bolus indicator device so that a patient has a clear indication whether or not a bolus of the liquid drug is ready to be administered.

SUMMARY OF THE INVENTION

In accordance with one embodiment of the present invention, a patient controlled drug administration device is provided. The patient controlled drug administration device includes an elongated push button, a plunger, a housing extending in an axial direction to define a top end and a bottom end, and a bolus refill indicator. The bolus refill indicator is disposed on the plunger and visible through a window located in the housing, wherein the bolus refill indicator includes a first section having a first color and located towards the top end of the housing, a second section having a second color and located towards the bottom end of the housing, and a third section disposed between the first section and the second section, wherein the third section includes a gradient between the first color and the second color.

In one embodiment, the bolus refill indicator can signal that a bolus is not ready for delivery when the first section of the bolus indicator device is visible through the window.

In another embodiment, the bolus refill indicator can signal that a bolus is not ready for delivery when the third section of the bolus indicator device is visible through the window.

In still another embodiment, the bolus refill indicator can signal that a bolus is ready for delivery when the second section of the bolus indicator device is visible through the window.

In yet another embodiment, the patient controlled drug administration device can include a first indicator reference point located on the housing and aligned with a bottom of the indicator window and a second indicator reference point located on the housing and aligned with a top of the indicator window. The first indicator reference point can be red, while the second indicator reference point can be green. Further, a bolus can be ready for delivery when the second section of the bolus refill indicator is aligned with the second indicator reference point. Meanwhile, a bolus is not ready for delivery when the first section, second section, or third section of the bolus refill indicator is aligned with the first indicator reference point.

In an additional embodiment, the first section of the bolus refill indicator can be red.

In one particular embodiment, the second section of the bolus refill indicator can be green.

In one more embodiment, the third section of the bolus refill indicator can transition from a red color adjacent the first section to a green color adjacent the second section.

In another embodiment, the bolus refill indicator can be movable with respect to the window as the elongated push button is depressed and the plunger contacts a pump to deliver a bolus of a liquid drug to the patient and can be movable as the elongated push button returns to an undepressed state and the plunger moves away from the pump as the pump refills with a new bolus of the liquid drug.

In accordance with another embodiment of the present invention, a patient controlled drug administration device is provided. The patient controlled drug administration device includes an elongated push button, a plunger, a housing extending in an axial direction, wherein the housing includes and a bolus refill indicator. The bolus refill indicator is disposed on the plunger and visible through a window located in the housing, wherein the bolus refill indicator includes an indicator line extending across an indicator body in a direction perpendicular to the axial direction in which the housing extends, and wherein a first indicator reference point that is a first color is located on the housing and aligned with a bottom of the indicator window and a second indicator reference point that is a second color is located on the housing and aligned with a top of the indicator window.

In one embodiment, the indicator line can be red.

In another embodiment, the first indicator reference point can be red and the second indicator reference point can be green.

In still another embodiment, a bolus can be ready for delivery when the indicator line of the bolus refill indicator is aligned with the second indicator reference point.

In yet another embodiment, the bolus is not ready for delivery when the indicator line of the bolus refill indicator is aligned with the first indicator reference point.

In an additional embodiment, the bolus refill indicator can be movable with respect to the window as the elongated push button is depressed and the plunger contacts a pump to deliver a bolus of a liquid drug to the patient and can be movable as the elongated push button returns to an undepressed state and the plunger moves away from the pump as the pump refills with a new bolus of the liquid drug.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE FIGURES

A full and enabling disclosure of the present invention to one skilled in the art, including the best mode thereof, is set forth more particularly in the remainder of the specification, including reference to the accompanying figures, in which.

Repeat use of reference characters in the present specification and drawings is intended to represent the same or analogous features or elements of the present invention.

DETAILED DESCRIPTION OF REPRESENTATIVE EMBODIMENTS

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a patient controlled drug administration device including an elongated push button, a plunger, a housing extending in an axial direction to define a top end and a bottom ends, and a bolus refill indicator. The indicator is disposed on the plunger and is visible through a window in the housing. The indicator can include a first section having a first color located towards the top end of the housing, a second section having a second color located towards the bottom end of the housing, and a third section disposed therebetween including a gradient between the first and second colors. Alternatively, the indicator can include a line extending in a direction perpendicular to the axial direction. The housing includes a first indicator reference point that is a first color and aligned with a bottom of the indicator window and a second indicator reference point that is a second color and aligned with a top of the indicator window. In any event, the combination of the spatial and colorimetric arrangement of the bolus refill indicator during the emptying and refilling of a pump disposed within the housing signals to a patient or user when a new bolus of a liquid drug is ready to be delivered in a clear, easy to understand manner without confusion.

Figure 1:
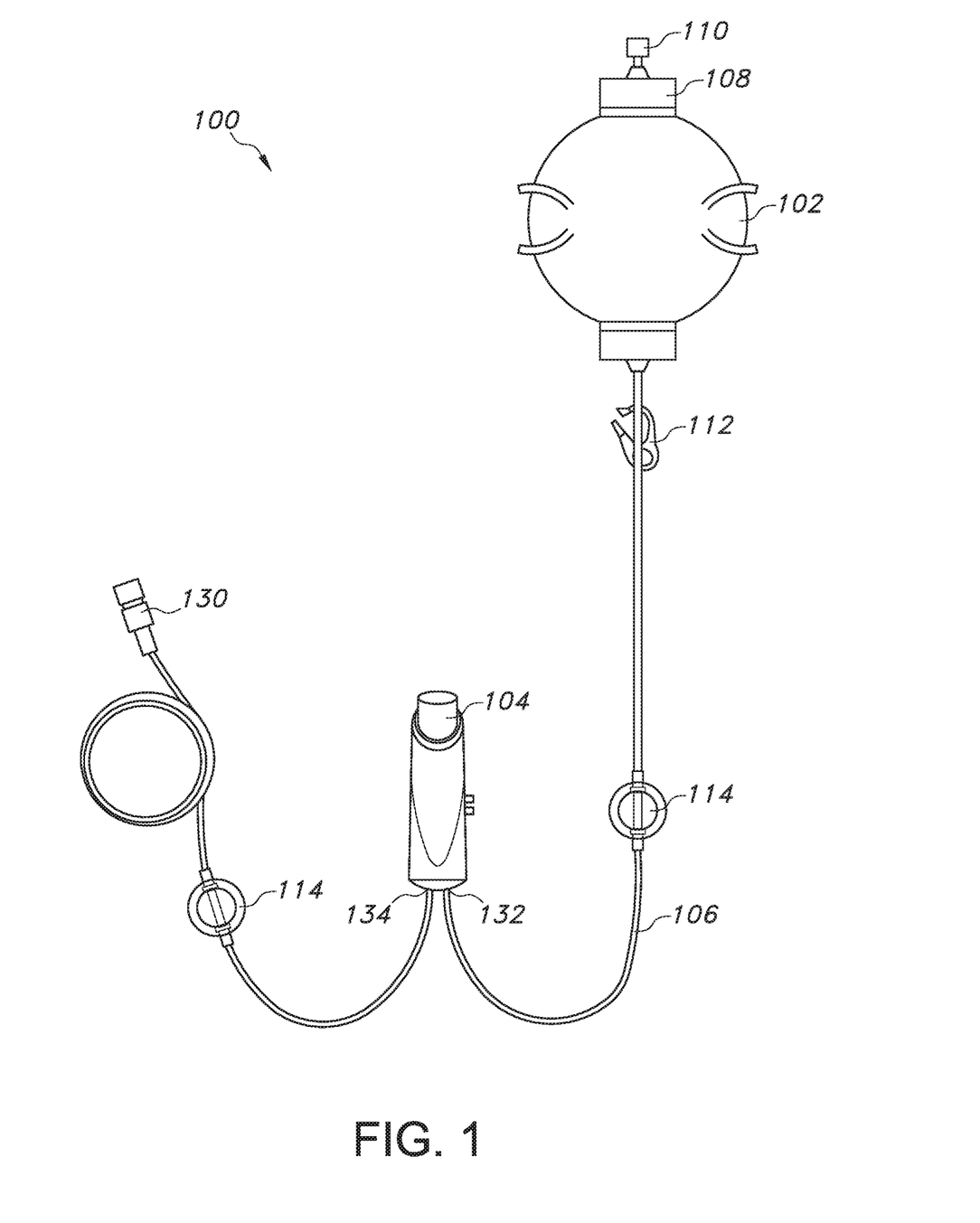
FIG. 1 illustrates a pain relief system that includes a patient controlled drug administration device that includes the bolus refill indicator of the present invention.

Referring to FIG. 1, a patient controlled drug administration device 104 with a bolus refill indicator 116 (see FIGS. 3-9C) can be used as a component of a pain relief system 100 that includes a pump 102, which can be filled with a liquid drug (e.g. an analgesic) via fill port 108 by removing fill cap 110. The pump 102 is connected to the patient controlled drug administration device 104 via tubing 106 at an inlet conduit 132. A clamp 112 can be used to control the flow of the drug from the liquid pump 102 to the patient controlled drug administration device 104 as needed. An air eliminating filter 114 can also be utilized in the pain relief system 100. The patient controlled drug administration device 104 also includes an outlet conduit 134, where tubing 106 extends from the outlet conduit 134 to a patient's catheter (not shown) by removing luer fitting 130 so that the patient can receive the liquid drug. The pump 102 is designed to provide continuous infusion (basal) of the liquid drug, while the patient controlled drug administration device 104 allows for the delivery of a fixed bolus of the liquid drug, where the delivery is "on demand" as needed by the patient or healthcare provider. As mentioned above and as discussed in more detail below, the patient controlled drug administration device 104 of the present invention includes a bolus refill indicator 116 (see FIGS. 3-9C) to effectively alert a patient or healthcare provider that the patient controlled drug administration device 104 is ready to deliver a full bolus of the liquid drug to the patient.

Figure 2:
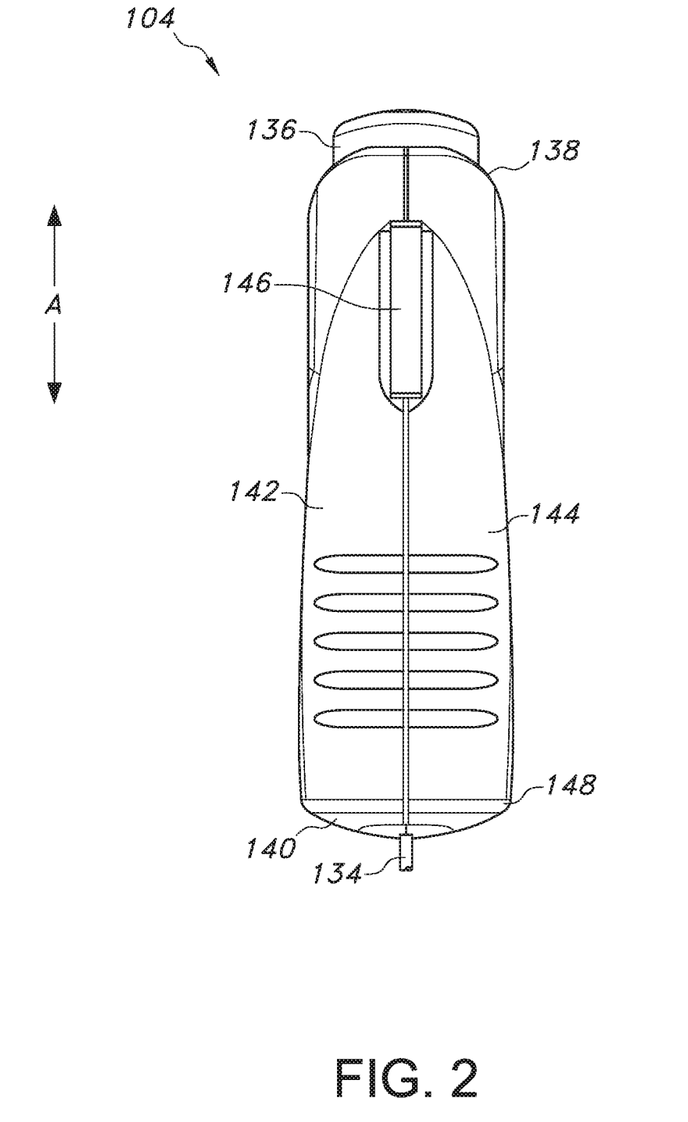
FIG. 2 is front view of the patient controlled drug administration device shown in FIG. 1.
Figure 3:
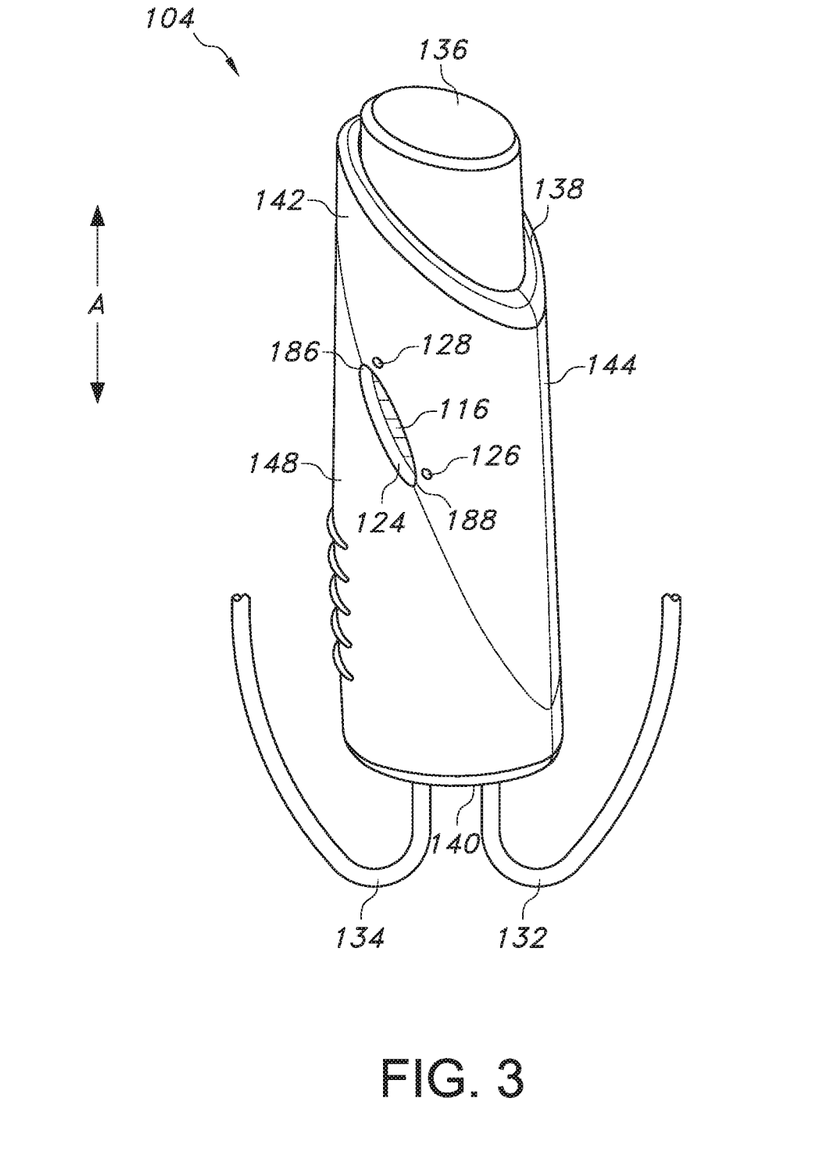
FIG. 3 is a perspective side view of the patient controlled drug administration device shown in FIG. 1.
Figure 4:
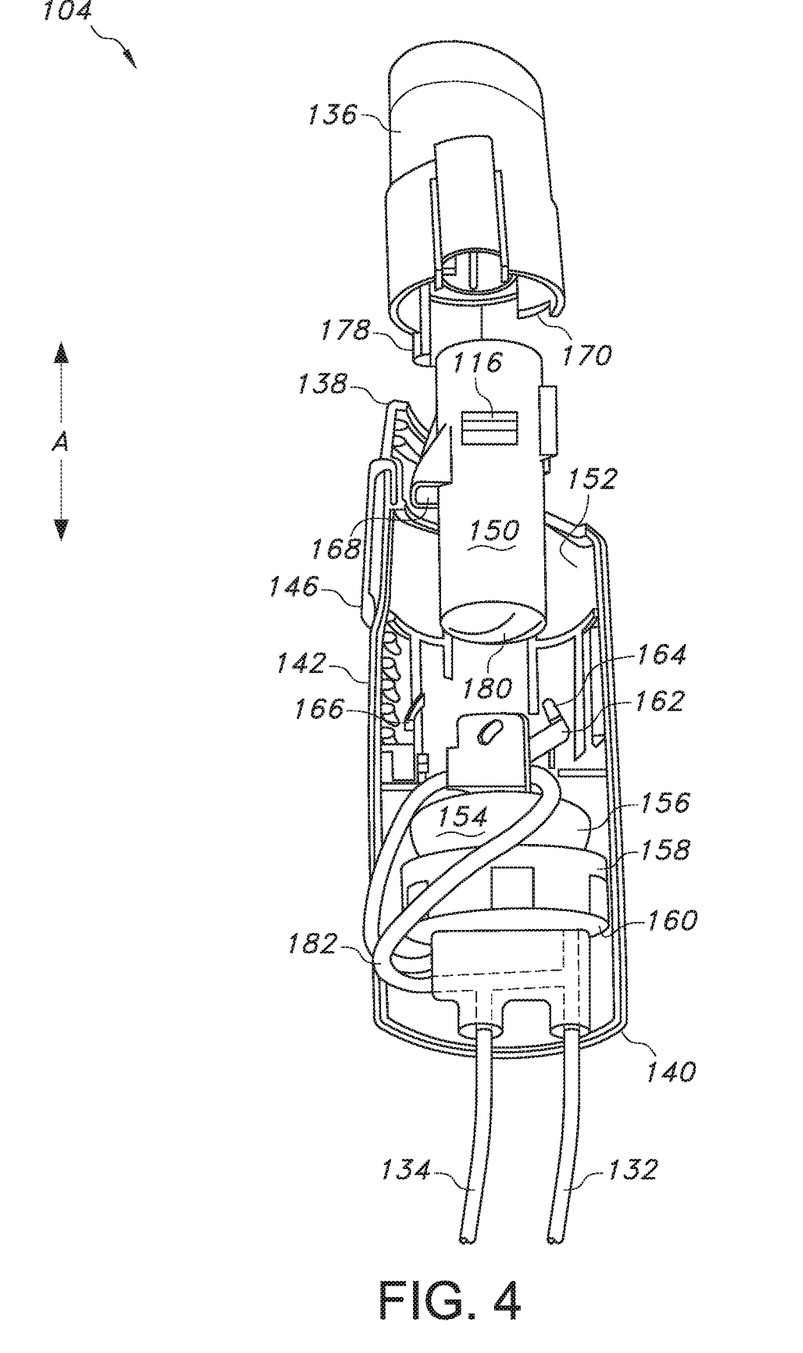
FIG. 4 is an exploded interior view of the patient controlled drug administration device shown in FIG. 1.

One particular embodiment of a patient controlled drug administration device that includes the bolus refill indicator of the present invention is shown in FIGS. 2-4. The patient controlled drug administration device 104 comprises an elongated housing 148 extending in the axial direction A and having respective open top and bottom ends 138 and 140 and an axial cavity 152 (see FIG. 4) extending through the housing 148. In the particular embodiment illustrated in the figures, the housing is injection molded from a rugged plastic material, and includes two clam-shell side walls 142 and 144 that are coupled together (e.g., with an adhesive) along a medial plane extending through the device.

As shown in FIG. 4, a reciprocating pump 160 is mounted in the cavity 152 of the housing 148 at the bottom end 140 thereof. The pump 160 defines a closed reservoir 154 for a liquid drug, and includes a first wall, or seat, 158 that is fixed in the cavity 152 against movement, and a second, flexible wall 156 that is axially movable in the cavity 152 with respect to the fixed wall 158 between a reservoir-full position and a reservoir-empty position.

The pump 160 includes an inlet and an outlet (not shown). One end of the inlet conduit 132 is connected to the inlet and the other end is connectable such as by means of a Luer fitting (not illustrated), to a source of a pressurized liquid drug (not illustrated), which can include an electromechanical infusion pump as known in the art. The outlet of the pump 160 is subcutaneously connectable, such as by a hypodermic needle (not illustrated) to the patient by the outlet conduit 134. In one particular embodiment, the inlet conduit 132 and the outlet conduit 134 comprise clear, flexible surgical tubing, and extend out the bottom end 140 of the housing 152 through a protective, flexible grommet (not shown).

A clamp 162 is mounted in the cavity 152 to move between a closed position constricting the outlet conduit 134, thereby preventing the flow of liquid through the conduit, and an open position disengaged from the outlet conduit 134, thereby allowing the flow of liquid through it. A spring (not shown) resiliently biases the clamp 162 toward its closed position. Closing the clamp blocks the outflow of the pump 160 so that the reservoir 154 takes in, or refills with, the pressurized liquid drug through the inlet of the pump 160, and that opening the clamp 162 enables the pump 160 to expel the contents of the reservoir 154 through the outlet of the pump 160.

In one particular embodiment, the clamp 162 comprises a lever arm (not shown) that is rotatably mounted on the side wall 144 of the housing 148 for movement between its closed and opened positions, and includes a wedge-shaped jaw (not shown) that constricts the outlet conduit 134 against an arcuate anvil on the side wall 144, over which a loop 182 of the outlet conduit 134 that is external to the pump 160 and internal to the housing 148 is led. A clamp shield (not shown) can serve to capture the internal portion of the outlet conduit 134 on the anvil and to journal the clamp 162 for rotational movement, as described in U.S. Pat. No. 6,936,035 to K. Rake et al.

As illustrated in FIG. 4, an elongated plunger 150 is captivated in the cavity 152 of the housing 148 above the pump 160 for axial movement between a raised position and a lowered position. The plunger 150 has a lower end 180 that contacts the movable wall 156 of the pump 160, and which has a shape that conforms to the internal shape of the fixed wall, or seat, 158 thereof. It may be seen that, if the clamp 162 is in its open position, a downward force exerted on the plunger 150 will cause the plunger 150 to move down from the raised position, and thereby push the movable wall 156 of the pump 160 toward the fixed wall 158 thereof, until the movable wall 156 conformably seats against the fixed wall 158, thereby executing an output stroke of the pump 160 and expelling a bolus of liquid drug from the reservoir 154 of the pump 160 to the patient. If the clamp 162 is then closed, the pressurized source of the drug will begin to fill the reservoir 154 with a new bolus of the drug, as above, causing the movable wall 156 to move away from the fixed wall 158, and conjointly raising the plunger 150 back up to its original, raised position, as described above.

The plunger 150 is pushed down by the patient indirectly through the agency of an elongated push button 136 that is captivated in the cavity 152 of the housing 148 above the plunger 150 for axial movement between an extended position (see FIGS. 7B and 9B) and a depressed position (see FIGS. 7A and 9A), as well as a compression spring (not shown) that is axially disposed between the plunger 150 and the button 136. The button 136 includes a detent 178 for latching the button 136 in the depressed position, and a ledge 170 that engages the clamp 162 and moves it to its open position when the button 136 is moved to its depressed position. When the button 136 is pushed to its depressed position, the ledge 170 of the button 136 engages an extension on the lever arm 164 of the clamp 162 and rotates it to its open position, thereby enabling outflow from the pump 160, as described above. Simultaneously, the latching detent 178 engages a resilient spring catch 166 mounted in the cavity 152 in an over-center latching engagement, which holds the button 136 in its depressed position and against the upward force of the compression spring.

Movement of the button 136 to its depressed position also compresses the compression spring against the plunger 150, resulting in a corresponding downward movement of the plunger 150 against the movable, flexible wall 156 of the pump 160 and a corresponding output stroke of the pump 160, as described above. Thus, a single, quick depression of the button 136 to its depressed position by the patient results in a subsequent full output stroke of the pump 160 that is typically of an extended duration, due to the flow resistance in the device between the pump 160 and the patient. However, since the button 136 latches in the depressed position, as above, it is unnecessary for the patient to exert a continuous force on the button 136 for the entire duration of the stroke.

To enable the button 136 to return automatically to its extended position at the end of the output stroke of the pump 160, a scoop-like catch release 168 is provided on the plunger 150 that catches an end of the spring catch 166 and detaches it from the latching detent 178 in the button 136 when the plunger 150 reaches its lowered position. When the button 136 returns to its extended position, the compression in the compression spring is relaxed, and simultaneously, the clamp 162 is released to return to its closed position, thereby initiating an intake stroke of the pump 160, as described above. Thus, the intake stroke of the pump 160 is effected automatically, and no activity or monitoring of the device 10 is required on the part of the patient.

As will be seen from the above, the patient controlled liquid drug administration device 104 enables a patient to self-administer successive, large-volume boluses of a liquid drug. Additionally, the pain management system 100 includes means by which the system is capable of administering a continuous, basal flow of the drug independently of patient control by the provision of a bypass conduit (not shown) on the pump 160 which can have a first end connected to the inlet conduit 132 upstream of the pump 160 and an opposite second end connected to the outlet conduit 134 downstream of the clamp 162. The flow of the liquid drug through the bypass conduit bypasses the reservoir 154 of the pump 160 and is thus administered directly to the patient through the outlet conduit 134. A flow restrictor (e.g., a glass orifice) can be provided in the bypass conduit for regulating the rate of basal or continuous flow of the liquid drug to the patient. Additionally, or alternatively, a second flow restrictor can be provided in the inlet conduit 132 of the pump 160 for regulating the rate at which the liquid drug refills the pump 160, and therefore, the maximum rate at which the patient can self-administer successive boluses of the drug, thereby precluding the possibility of a self-administered overdose thereof.

The patient controlled drug administration device 104 can also include a resilient clip 146 that can be provided on the housing 148 of the device 104 so that the device 104 can be conveniently attached to an article of the patient's clothing or bed clothes. Additionally, an indicator 116 is provided on an outer surface of the plunger 150, and a corresponding window 124 can be formed in one of the side walls 142 or 144 of the housing 148 of the device 104 through which the indicator 116 may be seen, such that the axial position of the plunger 150 relative to its raised (reservoir-full) and lowered (reservoir-empty) positions can be easily visualized through the housing 148. Various features and embodiments of the indicator 116 are discussed in more detail below.

Figure 5:
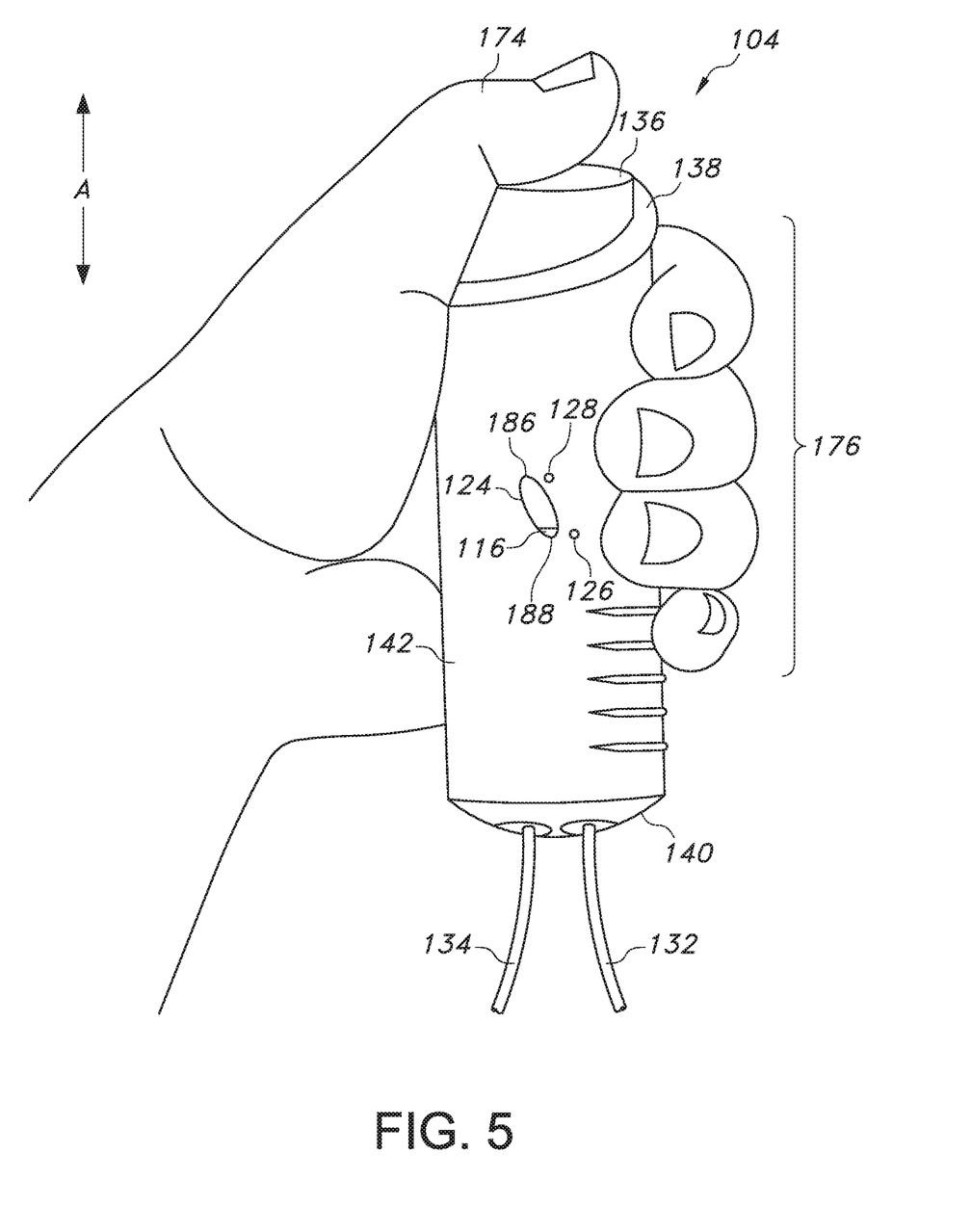
FIG. 5 illustrates the state of the patient controlled drug administration device shown in FIG. 1 as the button on the device is being depressed to deliver a bolus of a liquid drug to a patient.
Figure 6:
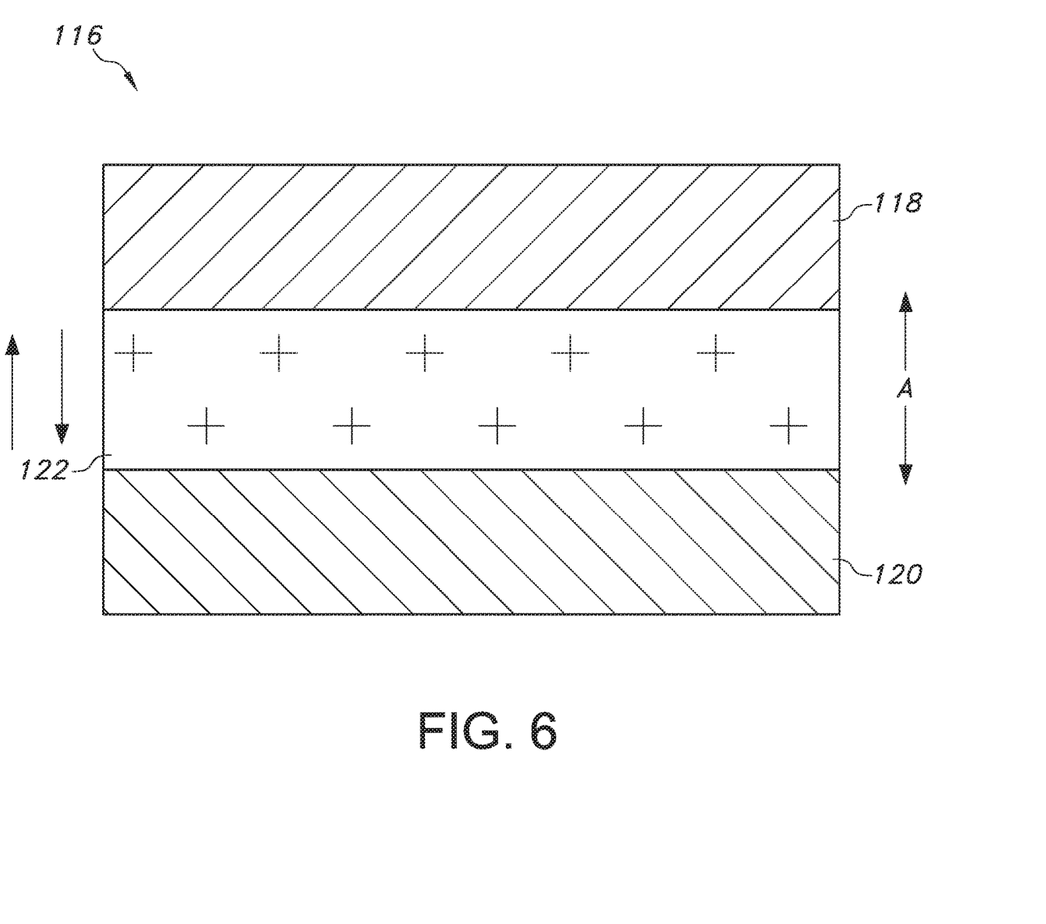
FIG. 6 illustrates one embodiment of a bolus refill indicator of the patient controlled drug administration device shown in FIG. 1 as contemplated by the present invention.

In particular reference to FIG. 5, the indicator 116 is visible via a window 124 even when a patient is grasping the patient controlled liquid drug administration device 104 during use to deliver a bolus of a liquid drug, where the patient is grasping the housing 148 with his or her palm (not shown) and fingers 176 and depressing the elongated push button 136 with his or her thumb 174 until it is flush with the top end 138 of the housing 148. Referring to FIGS. 4, 6, and 8, the indicator 116 itself can be square or rectangular, but the window 124 can be circular or oblong so that only a circular or oblong portion of the indicator 116 is visible from the exterior of the housing 148. As is shown in FIGS. 5, 7A-7C, and 9A-9C, the window 124 can be angled relative to the axial direction A in which the housing 148 extends. In addition, indicator reference points 126 and 128 can be present on the housing 148, where first indicator reference point 126 is located adjacent the window 124 towards the bottom end 140 of the housing and second indicator reference point 128 is located adjacent the window 124 towards the top end 138 of the housing 148. As discussed in more detail below with respect to FIGS. 7A-7C and 9A-9C, when a specific section of the indicator 116 is aligned with the first indicator reference point 126, the patient or user is informed that a bolus of liquid drug has been injected and a new bolus is not yet ready for delivery to the patient (i.e., the elongated push button 136 and plunger 150 are depressed). Meanwhile, when a specific section of the indicator 116 is aligned with the second indicator reference point 128, the patient or user is informed that a new bolus is not yet ready for delivery to the patient (i.e., the elongated push button 136 and plunger 150 are no longer depressed). In this regard, to further inform a patient or user about the status of the bolus of liquid drug, the first indicator reference point 126 can be a first color (e.g., red) and the second indicator reference point 128 can be a second color (e.g., green), where the alignment of a specific section of the indicator 116 with the first color 126 signals to the patient or user that a new bolus is not ready for delivery, and where the alignment of a specific section of the indicator 116 with the second color 128 indicates to the patient or user that new bolus is ready for delivery.

Figure 7A:
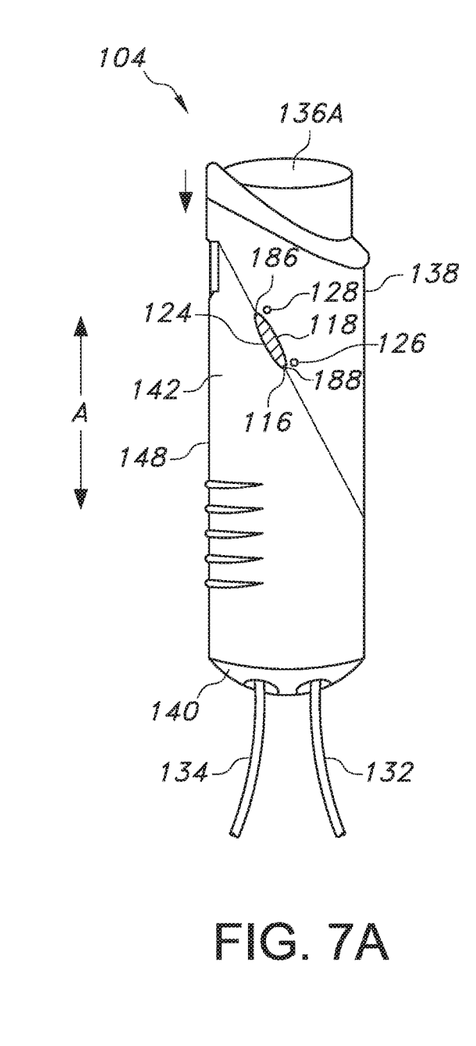
FIGS. 7A-7C illustrate the change in the bolus refill indicator of FIG. 6 as the button is of the patient controlled drug administration device is depressed for bolus delivery (FIG. 7A), as the button is in the process of moving upward as the drug pump refills (FIG. 7B), and when the button is at its highest point when the pump has been refilled and the bolus is ready for delivery (FIG. 7C)
Figure 7B:
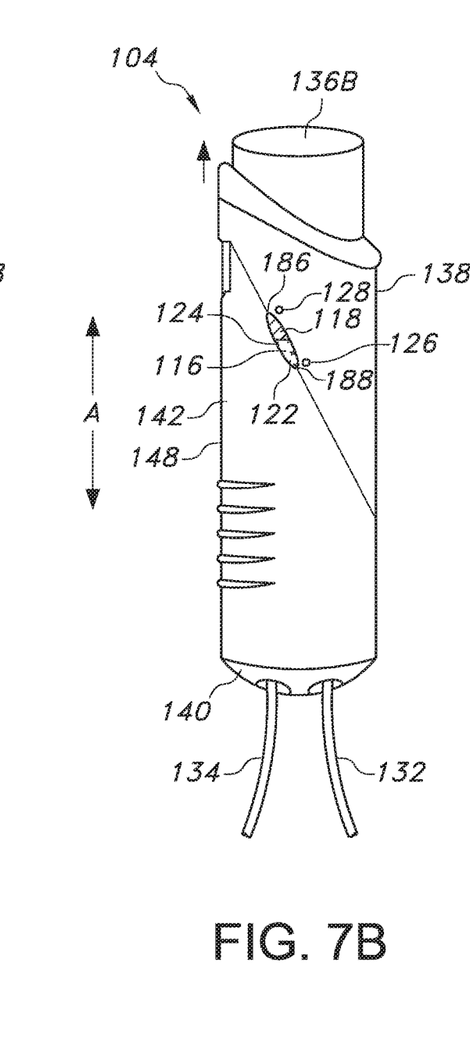
Figure 7C:
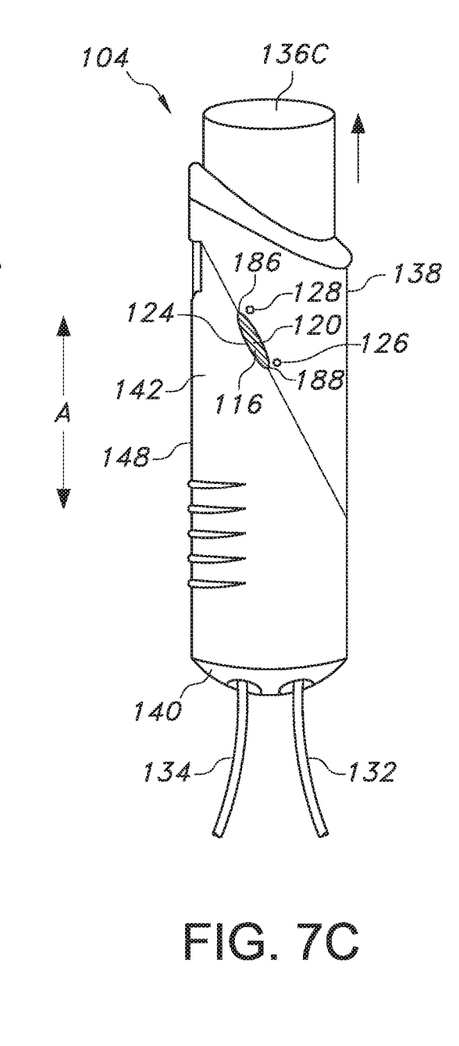
Figure 8:
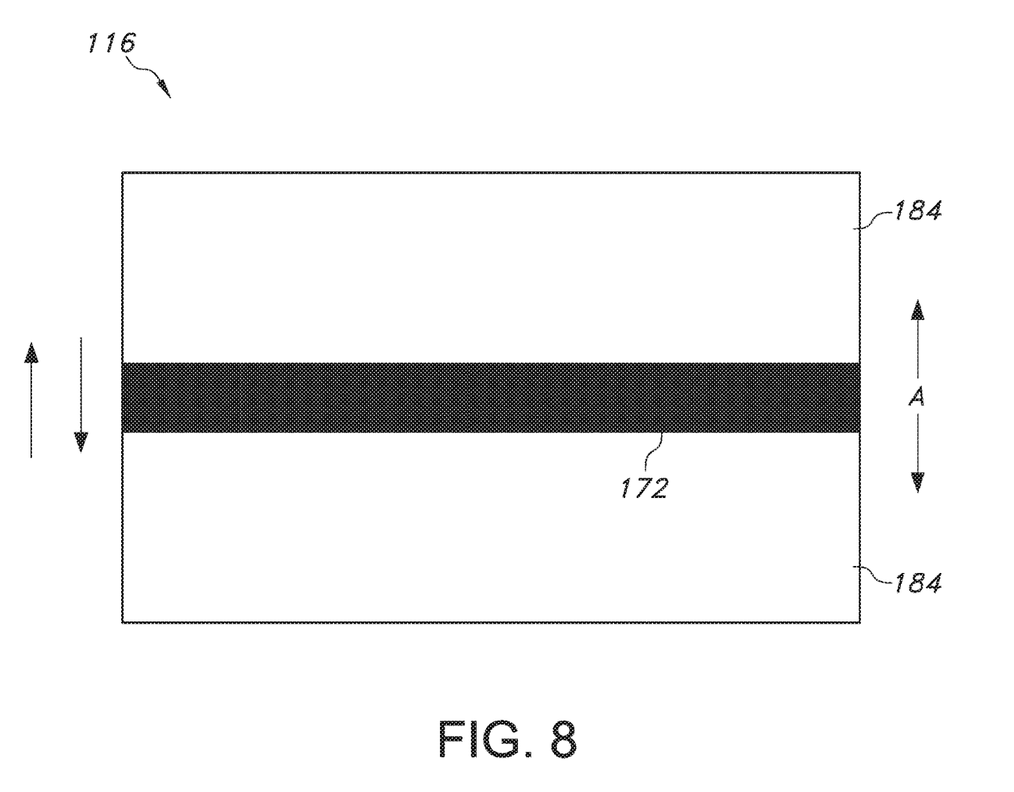
FIG. 8 illustrates another embodiment of the patient controlled drug administration device shown in FIG. 1 as contemplated by the present invention.

In one particular embodiment, the indicator 116 can be in the form of a series of three distinct sections 118, 120, and 122, as shown in FIGS. 6 and 7A-7C. In another particular embodiment, the indicator 116 can be in the form of a line 172, as shown in FIGS. 8 and 9A-9C. Turning first to FIG. 6, the indicator 116 can be in the form of a square or rectangle that has three distinct sections 118, 120, and 122. First section 118 can be a first color (e.g., red), second section 120 can be a second color (e.g., green), and third section 122, which is positioned between the first section 118 and the second section 120, can be in the form of a color gradient that transitions from the first color in the first section 118 to the second color in the second section 120 (e.g., a red to green gradient). As shown in FIG. 7A, when the elongated push button 136A is in a depressed state as a bolus of liquid drug is being administered to a patient, the first section 118 of the indicator 116 is visible in the window 124 in the housing 148 as a result of the plunger 150 being depressed downwards in the axial direction to compress the flexible wall 156 of the pump 160 from a reservoir-full position and a reservoir-empty position as the bolus of liquid drug is delivered. Then, as shown in FIG. 7B, when the elongated push button 136B is transitioning from a depressed state after the bolus of liquid drug is administered to a patient as the pump is refilling with the liquid drug to form a new bolus for delivery to the patient, the third section 122 of the indicator 116 is visible in the window 124 in the housing 148 as a result of the plunger 150 moving upwards from its depressed position in the axial direction as the flexible wall 156 of the pump 160 expands to a reservoir-full position from a reservoir-empty position. Next, as shown in FIG. 7C, once the elongated push button 136C is back in its original, undepressed position where the button 136C is at its highest point when the pump 160 has been refilled and a new bolus is ready for delivery to the patient, the second section 120 of the indicator 116 is visible in the window 124 in the housing 148 as a result of the plunger 150 having moved upwards in the axial direction as the flexible wall 156 of the pump 160 has expanded to its reservoir-full position from a reservoir-empty position. The present inventors have found that such colorimetric and spatial changes of the indicator 116 in the window 124 can provide a patient or user with improved awareness about the delivery status of a bolus of the liquid drug. For instance, when the first section (e.g., red section) 118 of the indicator 116 is visible in the window 124, a patient can be alerted that a bolus is not ready for delivery. Meanwhile, when the third section (e.g., gradient color change from red to green) 122 of the indicator 116 is visible in the window, a patient can be alerted that the pump 160 is in the process of refilling with the liquid drug and that the bolus is still not ready for delivery. Finally, when the second section (e.g., green section) 120 of the indicator 116 is visible in the window 124, a patient can be alerted that the pump 160 is full and that the bolus is ready for delivery.

Moreover, for additional reassurance regarding the status of a bolus, the housing 148 can include a first indicator reference point 126 having a first color (e.g., red) that is located on the housing 148 and aligned with the bottom 188 of the indicator window 124 and a second indicator reference point 128 having a second color (e.g., green) that is located on the housing 148 and aligned with the top 186 of the indicator window 124. When the second section (e.g., green section) 120 of the indicator 116 is visible in the window 124 and is also adjacent the second indicator reference point 128, a patient can have further assurance that the pump 160 is full and that the bolus is ready for delivery. Meanwhile, the patient is informed that the pump 160 is not full and that the bolus is not ready for delivery if any other section (e.g., first section 118 or third, gradient section 122) of the indicator 116 is adjacent the second indicator reference point 128 or if any section (e.g., first section 118, second section 120, or third, gradient section 122) of the indicator 116 is adjacent the first indicator reference point 126.

Figure 9A:
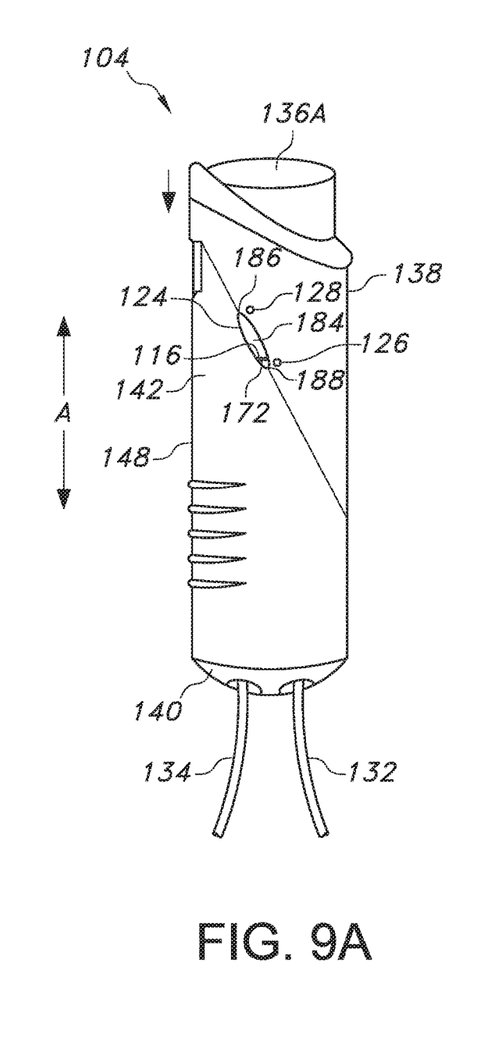
FIGS. 9A-9C illustrate the change in the bolus refill indicator of FIG. 8 as the button is of the patient controlled drug administration device id depressed for bolus delivery (FIG. 9A), as the button is in the process of moving upward as the drug pump refills (FIG. 9B), and when the button is at its highest point when the pump has been refilled and the bolus is ready for delivery (FIG. 9C).
Figure 9B:
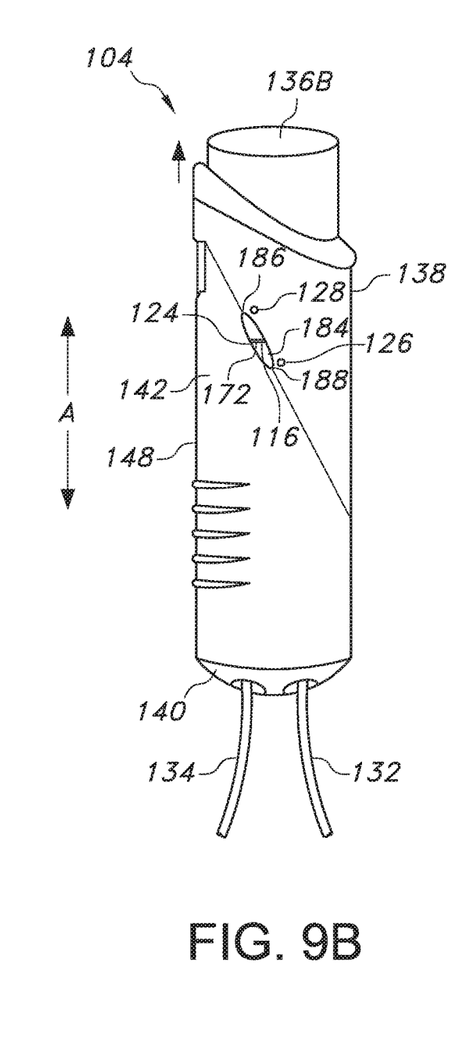
Figure 9C:
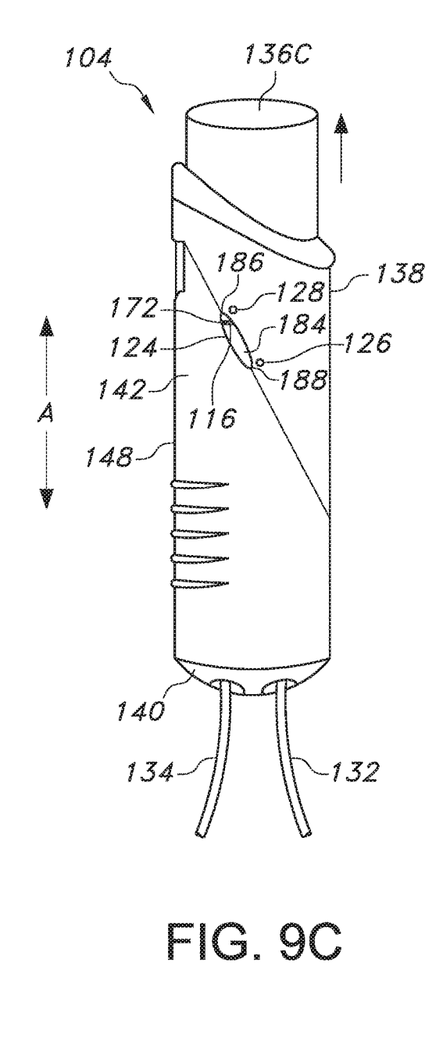

In another embodiment, the indicator 116 can include an indicator line 172 having a first color (e.g., red) where the body 184 of the indicator 116 surrounding the indicator line 172 exhibits a second color (e.g., white, cream, clear, etc.), as shown in FIGS. 8 and 9A-9C. Specifically, the indicator line 172 can be positioned in a middle section of the indicator 116 and can be positioned perpendicular to the axial direction A in which the housing 148 extends. As shown in FIG. 9A, when the elongated push button 136A is in a depressed state as a bolus of liquid drug is being administered to a patient, the indicator line 172 is visible in the window 124 adjacent a first indicator reference point 126 having a first color (e.g., red) that is located on the housing 148 and aligned with the bottom 188 of the indicator window 124, as a result of the plunger 150 being depressed downwards in the axial direction to compress the flexible wall 156 of the pump 160 from a reservoir-full position and a reservoir-empty position as the bolus of liquid drug is delivered. Then, as shown in FIG. 9B, when the elongated push button 136B is transitioning from a depressed state after the bolus of liquid drug is administered to a patient as the pump is refilling with the liquid drug to form a new bolus for delivery to the patient, the indicator line 172 is visible in a middle section of the window 124 neither adjacent the first indicator reference point 126 nor the second indicator reference point 128 located on the housing 148, as a result of the plunger 150 moving upwards from its depressed position in the axial direction as the flexible wall 156 of the pump 160 expands to a reservoir-full position from a reservoir-empty position. Next, as shown in FIG. 9C, once the elongated push button 136C is back in its original, undepressed position where the button 136C is at its highest point when the pump 160 has been refilled and a new bolus is ready for delivery to the patient, the indicator line 172 is visible in the window 124 adjacent a second indicator reference point 128 having a second color (e.g., green) that is located on the housing 148 and aligned with the top 186 of the indicator window 124, as a result of the plunger 150 having moved upwards in the axial direction as the flexible wall 156 of the pump 160 has expanded to its reservoir-full position from a reservoir-empty position. The present inventors have found that such colorimetric and spatial changes in the window 124 can provide a patient or user with improved awareness about the delivery status of a bolus of the liquid drug. For instance, when the indicator line 172 is adjacent and aligned with the lower, first indicator line reference point 126, where the indicator line 172 and the first indicator line reference point 126 can be the same color (e.g., red), a patient can be alerted that a bolus is not ready for delivery. Meanwhile, when the indicator line 172 is present in an area of the window 124 such that it is not aligned with or adjacent the first indicator line reference point 126 or the second indicator line reference point 128, a patient can be alerted that the pump 160 is in the process of refilling with the liquid drug and that the bolus is still not ready for delivery. Finally, when the indicator line 172 is adjacent and aligned with the upper, second indicator line 128, where the indicator line 172 and the second indicator line reference point 128 are different colors (e.g. the indicator line 172 is red and the second indicator line reference point 128 is green), a patient can be alerted that the pump 160 is full and that the bolus is ready for delivery.

By selecting the colors red and green, which are generally associated with "stop/wait" and "go," respectively, a patient can have increased reassurance about the status of the bolus for delivery as compared to the use of other colors, such as yellow or orange. In combination with a spatial change of the indicator 116 in the axial direction from the bottom of the indicator window 124 to the top 186 of the indicator window 124, the use of a red first indicator reference point 126 on the housing 148 adjacent and aligned with the bottom 188 of the indicator window 124 and a green second indicator reference point 128 on the housing 148 adjacent and aligned with the top 186 of the indicator window 124 provides further assurance a patient or user that a bolus is not ready (when the indicator line 172 is aligned at the bottom 188 of the indicator window 124 with red first indicator line reference point 126) or that the bolus is ready (when the indictor line 172 is aligned at the top 186 of the indicator window 124 with green second indicator line reference point 128).

The present invention has been described both in general and in detail by way of examples. These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A patient controlled drug administration device comprising:
   an elongated push button, a plunger, a housing extending in an axial direction to define a top end and a bottom end, and a bolus refill indicator, wherein the bolus refill indicator is disposed on the plunger and visible through a window located in the housing, wherein the bolus refill indicator includes a first section having a first color and located towards the top end of the housing, a second section having a second color and located towards the bottom end of the housing, and a third section disposed between the first section and the second section, wherein the third section includes a gradient between the first color and the second color, wherein the bolus refill indicator is movable with respect to the window such that the first color is visible when the elongated push button is depressed and the plunger contacts a pump to deliver a bolus of a liquid drug to the patient, the gradient is visible as the elongated push button returns to an undepressed state and the plunger moves away from the pump as the pump refills with a new bolus of the liquid drug, and the second color is visible when the elongated push button fully returns to the undepressed state, and wherein the spatial and colorimetric arrangement of the first section, the second section, and the third section of the bolus refill indicator signals to a user when the new bolus of the liquid drug is ready for delivery.

2. The patient controlled drug administration device of claim 1, wherein the bolus refill indicator signals that the new bolus is not ready for delivery when the first section of the bolus refill indicator is visible through the window.

3. The patient controlled drug administration device of claim 1, wherein the bolus refill indicator signals that the new bolus is not ready for delivery when the third section of the bolus refill indicator is visible through the window.

4. The patient controlled drug administration device of claim 1, wherein the bolus refill indicator signals that the plunger has moved away from the pump and the pump refilled such that the new bolus is ready for delivery when the second section of the bolus refill indicator is visible through the window.

5. The patient controlled drug administration device of claim 1, further comprising a first indicator reference point located on the housing and aligned with a bottom of the window and a second indicator reference point located on the housing and aligned with a top of the window.

6. The patient controlled drug administration device of claim 5, wherein the first indicator reference point is red and the second indicator reference point is green.

7. The patient controlled drug administration device of claim 5, wherein the new bolus is ready for delivery when the second section of the bolus refill indicator is aligned with the second indicator reference point.

8. The patient controlled drug administration device of claim 5, wherein the bolus is not ready for delivery when the first section, second section, or third section of the bolus refill indicator is aligned with the first indicator reference point.

9. The patient controlled drug administration device of claim 1, wherein the first section of the bolus refill indicator is red.

10. The patient controlled drug administration device of 1, wherein the second section of the bolus refill indicator is green.

11. The patient controlled drug administration device of 1, wherein the third section of the bolus refill indicator transitions from a red color adjacent the first section to a green color adjacent the second section.

12. A patient controlled drug administration device comprising:

an elongated push button, a plunger, a housing extending in an axial direction, wherein the housing includes a bolus refill indicator, wherein the bolus refill indicator is disposed on the plunger and visible through a window located in the housing, wherein the bolus refill indicator includes an indicator line extending across an indicator body in a direction perpendicular to the axial direction in which the housing extends, and wherein a first indicator reference point that is a first color is located on the housing and aligned with a bottom of the indicator window and a second indicator reference point that is a second color is located on the housing and aligned with a top of the indicator window, wherein the bolus refill indicator is movable with respect to the window such that the first color is visible when the elongated push button is depressed and the plunger contacts a pump to deliver a bolus of a liquid drug to the patient, the gradient is visible as the elongated push button returns to an undepressed state and the plunger moves away from the pump as the pump refills with a new bolus of the liquid drug, and the second color is visible when the elongated push button fully returns to the undepressed state, and wherein the spatial and colorimetric arrangement of the indicator line, the first indicator reference point and the second indicator reference point of the bolus refill indicator signals to a user when the new bolus of the liquid drug is ready for delivery.

13. The patient controlled drug administration device of claim 12, wherein a bolus is ready for delivery when the indicator line of the bolus refill indicator is aligned with the second indicator reference point, wherein the bolus is not ready for delivery when the indicator line of the bolus refill indicator is aligned with the first indicator reference point.

14. The patient controlled drug administration device of claim 12, wherein the bolus refill indicator is movable with respect to the window as the elongated push button is depressed and the plunger contacts a pump to deliver the new bolus of a liquid drug to the patient and as the elongated push button returns to an undepressed state and the plunger moves away from the pump as the pump refills with a new bolus of the liquid drug.

15. The patient controlled drug administration device of claim 1, wherein the first section is visible when the elongated push button is flush with the top end of the housing.

16. The patient controlled drug administration device of claim 1, wherein the pump further comprises a flexible wall that abuts the plunger and compresses to empty the bolus out of the pump when the first section of the bolus refill indicator is visible through the window.

17. The patient controlled drug administration device of claim 16, wherein the flexible wall expands to refill the pump with the new bolus when the second section of the bolus refill indicator is visible through the window.

* * * * *